United States Patent [19]
Taguchi et al.

[11] Patent Number: 4,909,789
[45] Date of Patent: Mar. 20, 1990

[54] OBSERVATION ASSISTING FORCEPS

[75] Inventors: Akihiro Taguchi; Akira Shiga, both of Hachioji, Japan

[73] Assignee: Olympus Optical Co., Ltd., Tokyo, Japan

[21] Appl. No.: 29,571

[22] Filed: Mar. 24, 1987

[30] Foreign Application Priority Data

Mar. 28, 1986 [JP] Japan .................................. 61-070229
May 15, 1986 [JP] Japan .................................. 61-111923
Jun. 6, 1986 [JP] Japan .................................. 61-131464

[51] Int. Cl.$^4$ ............................................. A61L 17/11
[52] U.S. Cl. ...................................... 604/107; 606/198
[58] Field of Search ............... 604/103, 104, 105, 106, 604/107; 128/345, 343

[56] References Cited

U.S. PATENT DOCUMENTS

| | | | |
|---|---|---|---|
| 3,467,090 | 9/1969 | Zollett ................................. | 602/102 |
| 4,557,255 | 12/1985 | Goodman ........................... | 128/345 |
| 4,598,699 | 7/1986 | Garren et al. . | |
| 4,654,028 | 3/1987 | Suma .................................. | 604/107 |
| 4,655,219 | 4/1987 | Petruzzi ............................. | 128/321 |
| 4,692,139 | 9/1987 | Stiles ................................. | 604/109 |

FOREIGN PATENT DOCUMENTS

| | | | |
|---|---|---|---|
| 83033424 | 7/1983 | Fed. Rep. of Germany . | |
| 468805 | 3/1953 | Italy .................................. | 604/107 |
| 52-52388 | 4/1977 | Japan . | |
| 53-94481 | 8/1978 | Japan . | |
| 54-63992 | 5/1979 | Japan . | |
| 57-193811 | 12/1982 | Japan . | |

*Primary Examiner*—Carl Stuart Miller
*Attorney, Agent, or Firm*—Armstrong, Nikaido, Marmelstein, Kubovcik & Murray

[57] ABSTRACT

Observation assisting forceps wherein a shaft member is retractably inserted through a hollow sheath, a plurality of linear members given a characteristic of expanding on the tip sides are provided at the front end of this shaft member and spherical parts are provided at the tips of the respective linear members so that the linear members may be projected on the tip sides out of the sheath tip to move aside any organ or the like obstructing the observation with an endoscope.

6 Claims, 7 Drawing Sheets

OBSERVATION ASSISTING FORCEPS

BACKGROUND OF THE INVENTION

Field of the Invention and Related Art Statement

This invention relates to observation assisting forceps adapted to assist the observation with an endoscope by moving an internal organ to a place easy to observe by projecting linear or rod-shaped members expanding out of a sheath.

Recently there has come to be extensively used an endoscope with which the interior of a body cavity can be observed or treated to be cured with treating devices by inserting an elongate insertion part without incising the body from the surface.

The above mentioned endoscope is a flexible endoscope wherein the insertion part is flexible and is inserted through the mouth cavity or the like or a rigid endoscope wherein the insertion part is rigid and is inserted toward an object position to be observed within a body cavity as guided by such sting as a trocar.

Now, a rigid endoscope to be used to observe mostly an abdominal part, that is, an abdominal cavity endoscope had to be moved with forceps or probes to a place easy to observe the interior of an abdominal cavity or particularly such female organ as a womb, salpinx or ovary in the case of observing it. For example, in order to observe the ovary hidden behind the womb and salpinx, it is necessary to set aside the womb and salpinx. In such case, as disclosed in the prior art examples of Japanese Utility Models Laid Open Nos. 193811/1982 and 63992/1979, the salpinx is grasped with ordinary grasping forceps and is set aside or the salpinx and womb are pressed with an ordinary probe and is set aside in order to observe the ovary.

However, when the salpinx is grasped freely with such grasping forceps as in the above mentioned prior art example, the salpinx will be likely to be hurt. It is in fact unreasonable to grasp such large organ as the womb. The probe is a mere rod-shaped probe. It is difficult with this one probe to move such large organ as the womb to a required place or to keep it set aside.

Also, in German Utility Model No. G8303342.4, there is disclosed a prior art example wherein a plurality of grasping arms are inserted through a sheath and are projected out of the tip of the sheath by the operation of a handle on the holding side to grasp an organ to be observed with an endoscope.

In this prior art example, as the arms are inserted through the sheath through which the endoscope is inserted, it is difficult with the arms to set aside another organ obstructing the observation of an organ to be observed with the endoscope.

OBJECTS AND SUMMARY OF THE INVENTION

An object of the present invention is to provide observation assisting forceps which can move an organ obstructing the observation with an endoscope.

Another object of the present invention is to provide observation assisting forceps which can move an organ obstructing the observation without hurting the organ.

According to the present invention, a shaft member is retractably inserted through a hollow sheath, a plurality of linear members energized to expand on the tip sides are provided at the tip of this sheath member and spherical parts which will not hurt an organ even when pressed against it are provided at the tips of the respective linear members so that, when the linear members are projected out of the tip of the sheath, an organ obstructing the observation will be able to be moved aside without being hurt and a desired position or the like will be able to be observed.

BRIEF DESCRIPTION OF THE DRAWINGS

FIG. 1 is a sectioned view showing the tip side of the first embodiment as expanded.

FIG. 2 is a sectioned view showing the entirety of the first embodiment.

FIG. 3 is a sectioned view on line A—A' in FIG. 1.

FIG. 4 is a sectioned view showing the first embodiment as the element wires on the tip side are projected out of the tip of the sheath.

FIG. 5 is an explanatory view showing a using example of the first embodiment.

FIG. 10 is a sectioned view of a removing apparatus.

FIG. 11 is a sectioned view on line B—B' in FIG. 10.

FIG. 12 is a sectioned view of the tip side of the removing apparatus as used.

FIG. 14 is a sectioned view of a binding thread holder.

FIG. 15 is a right side view of FIG. 14.

FIG. 16 is an elevation of a binding thread.

FIG. 17 is a sectioned view of the grasping apparatus.

FIG. 18 is an explanatory view of the using state.

FIG. 21 is a sectioned view of the tip side of the grasping apparatus.

FIG. 22 is a sectioned view on line X—X' in FIG. 21.

DETAILED DESCRIPTION OF PREFERRED EMBODIMENTS

Figure 1:
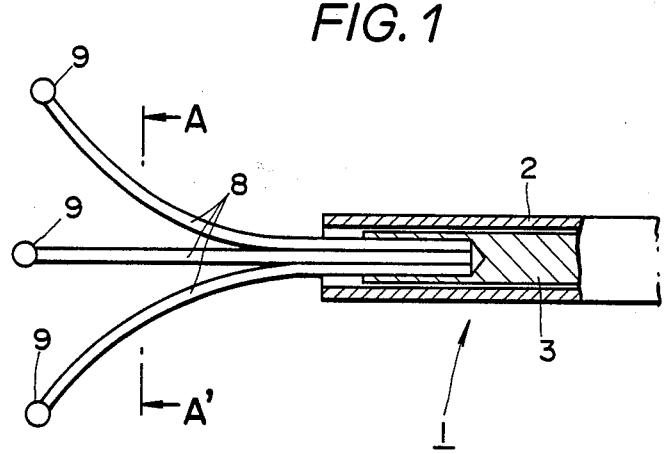
FIGS. 1 to 5 relate to the first embodiment of the present invention.
Figure 3:
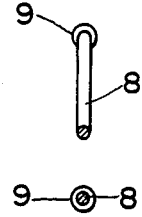
Figure 2:
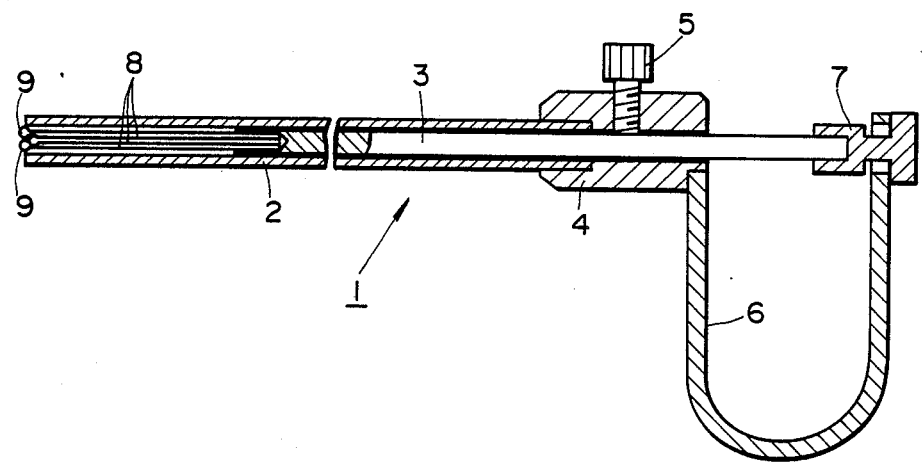
Figure 4:
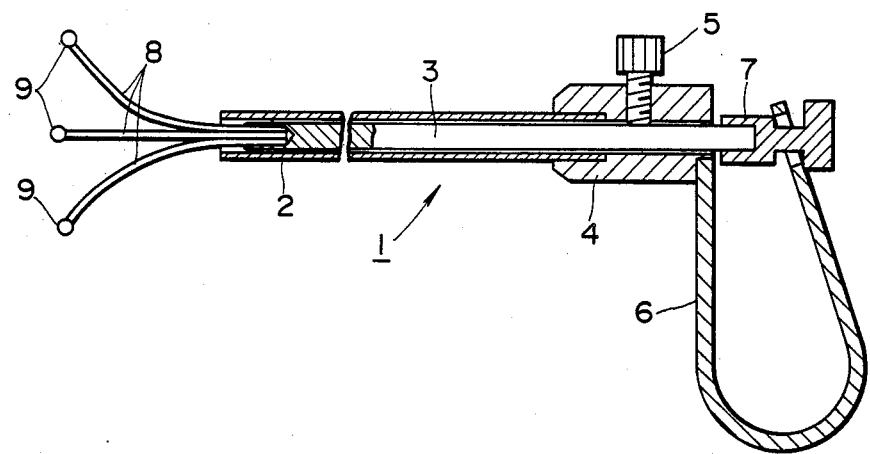
Figure 5:
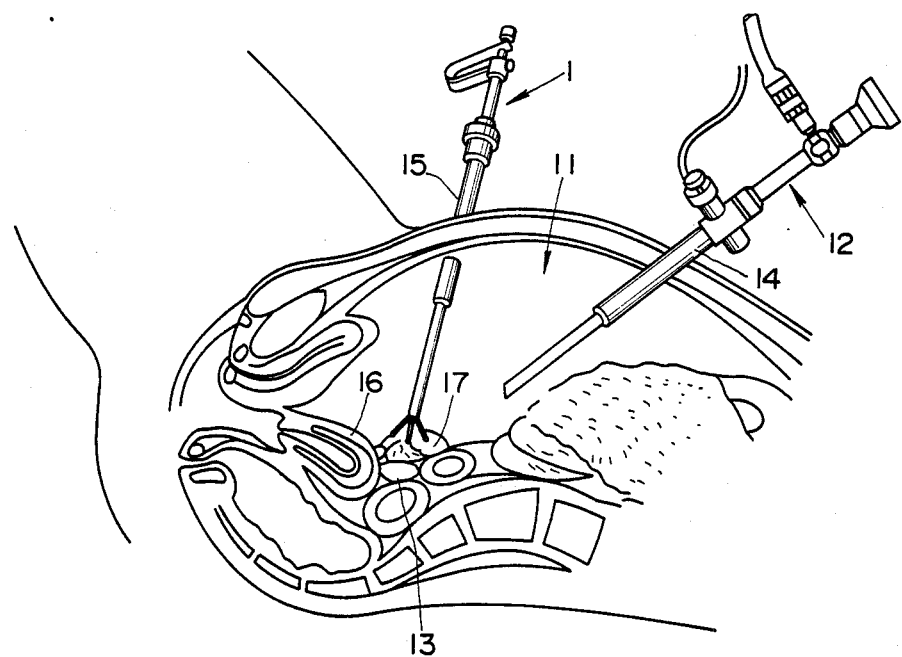

As shown in FIG. 2 or 5, in observation assisting forceps 1 of the first embodiment, a shaft 3 of a small diameter is retractably inserted through an elongate hollow sheath 2 which is cemented at the rear end to an operating part body 4. In this operating part body 4, a set screw 5 is screwed in a screw hole leading from the upper side to the hollow path (of the operating part body 4) to fix the shaft 3 retractable through this hollow path so as not to move. A plate spring 6 curved, for example, to be U-shaped is secured at one end to the lower side of this operating part body 4 and is fixed at the other end to a plate spring fixing member 7. This fixing member 7 is passed on the front end side through a through hole of the plate spring 6 and is then fixed by cementing or screwing to the rear end of the shaft 3. The shaft 3 is energized by this plate spring 6 in the direction of moving rearward. As shown in FIGS. 1 to 3, three element wires 8 as observation assisting pieces are cemented at the rear ends by cementing or the like to the front end of the shaft 3 and are fitted at the tips with spherical members 9 by integral formation, screwing or brazing so as not to hurt an organ or the like even in case the element wires 8 are pressed at the tips. The above mentioned three linear or rod-shaped element wires 8 are given a characteristic (habit) of expanding on the front end sides to be fan-shaped in the same plane. Therefore, when the shaft 3 is energized by the plate spring 6 to move rearward, the three element wires 8 will be retracted (contained) in the sheath 2 as shown in FIG. 2. When the U-shaped part of this plate spring 6 is gripped to be bent in the direction of bringing both ends of U close to each other against the energizing force, the shaft 3 will be slid forward to be in the state shown in FIG. 4 and the three element wires 8 will be able to be projected out of the sheath 2 as shown in FIG. 4 or 1. As the three projected element wires are given a characteristic of expanding to be fan-shaped, these three element wires 8 will expand to be fan-shaped in the same plane as shown in FIG. 3. Internal organs obstructing the observation with an abdominal cavity endoscope can be simply set aside by these expanded element wires 8. As the shaft 3 can be fixed with the set screw 5 in the operating part body 4, the projected amount of the element wires 8 (out of the sheath 2) can be fixed at any amount and the size of the fan formed by the element wires 8 can be freely set. Therefore, when the size of the fan shape is varied and set in response to the organ, any organ of a different size will be able to be handled.

The using example of the thus formed first embodiment shall be explained in the following with reference to FIG. 5.

FIG. 5 shows a female abdominal cavity 11 as an ovary 13 or the like is observed with an abdominal cavity endoscope 12.

The abdominal cavity endoscope 12 is inserted into the abdominal cavity 11 through a first trocar 14. The observation assisting forceps 1 of the first embodiment are inserted into the abdominal cavity 11 through a second trocar 15. In case a womb 16 or salpinx 17 obstruct the observation of the ovary 13, with the element wires 8 expanded to be fan-shaped by moving the shaft 3 forward, the womb 16 or salpinx 17 may be simply set aside and may be kept pressed as it is or the object to be observed may be lifted as mounted on the element wires expanded to be fan-shaped so as to be set in a state easy to observe. In such case, by fixing the shaft 3 with the set screw 5, the size of the fan shape can be varied and set in response to the organ to be handled and therefore any organ different in the size can be extensively handled. As the respective element wires 8 are provided at the tips respectively with spherical members 9, even if the element wires 8 are pressed at the tips against an organ, the organ will be able to be prevented from being hurt.

When the salpinx 17 is set aside to be outside the observed visual field and is simply kept as it is with the element wires 8 expanded to be fan-shaped as shown in FIG. 5, the ovary 13 below the salpinx 17 will be able to be observed with the endoscope 12.

Figure 6:
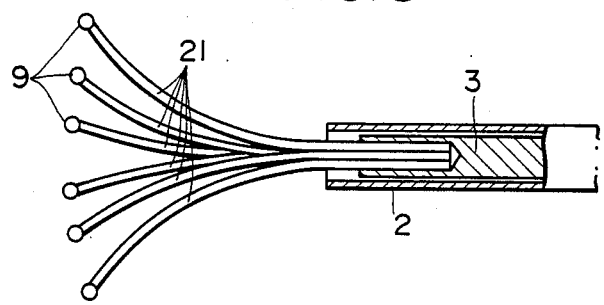
FIG. 6 is a sectioned view showing the tip side of the second embodiment of the present invention.

FIG. 6 shows the tip side of the second embodiment of the present invention.

In this second embodiment, six element wires 21 are fitted to the front end of the shaft 3 of the first embodiment. These element wires 21 are given such habit as of expanding to be substantially fan-shaped in the same plane in case they are projected out of the sheath 2 the same as in the first embodiment. In this second embodiment, the spacing between the adjacent element wires 21 is so narrow that, in case such comparatively thin or small organ as a salpinx is to be handled, the organ can be prevented from dropping between the element wires 21 and is easy to move and observe.

Figure 7:
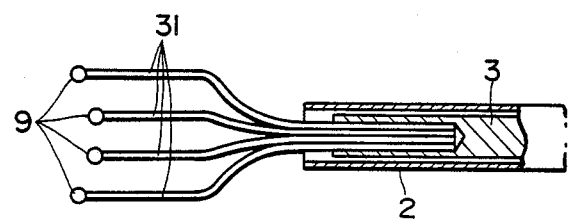
FIG. 7 is a sectioned view showing the tip side of the third embodiment of the present invention.

FIG. 7 shows the tip side of the third embodiment of the present invention.

In this third embodiment of the present invention, the shaft 3 is fitted on the front end side with four element wires 31 made to show a characteristic of expanding to be parallelly arranged on the front end side substantially in the same plane.

A plurality of element wires may expand in some range substantially in the same plane and may be of any other shape than the fan shape.

Figure 8:
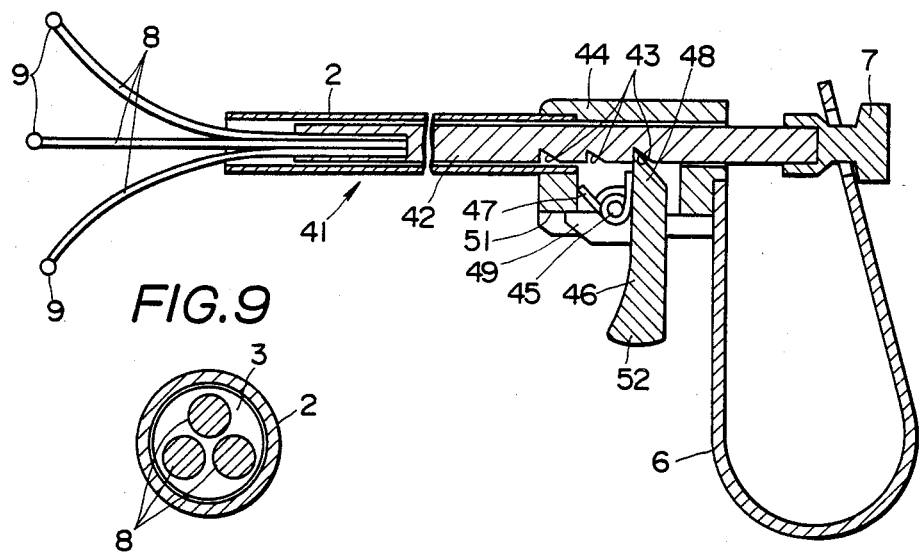
FIG. 8 is a sectioned view showing the fourth embodiment of the present invention.

FIG. 8 shows the fourth embodiment of the present invention.

In observation assisting forceps 41 of this fourth embodiment, there is formed a fixing means by a ratchet instead of the set screw 5 in the first embodiment.

That is to say, a shaft 42 is inserted through the sheath 2. Wedge-shaped incisions 43 are made in several places (three places in this example) on the underside near the rear end of this shaft 42.

On the other hand, the operating part body 44 is provided in the part opposed to the shaft 42 with a pin 45 to project. This pin 45 is passed through a through hole of a locking member 46 which is thus rotatably pivoted. In this locking member 46, a coil spring 47 fitted around the above mentioned pin 45 is contacted at one end with the operating part body 44 and is made at the other end to press the locking member 46 to energize the locking member 46 to rotate clockwise around the pin 45 as a center. This locking member 46 is provided at the upper end with a first pawl 48 engaging with the above mentioned incisions 43 and is provided in the forward direction intersecting at right angles with this first pawl with a second pawl 49 to project. This second pawl 49 contacts an incised surface 51 of the operating part body 44 so as to be regulated in the rotary movement. By the way, a trigger part 52 is formed of the underside part pivoted with this pin 45 of the above mentioned locking member 46.

The others are substantially the same as in the above mentioned first embodiment.

In the thus formed fourth embodiment, when the shaft 42 is projected forward against the energizing force of the plate spring 6, the first pawl 48 of the locking member 44 will fit into one of the incisions 43 of the shaft 42. When this pawl 48 fits in the incision 43, even if the force pushing out the shaft 42 forward is released, the second pawl 49 of the locking member 46 will collide with the body 44 and the shaft 42 will be locked by the locking member 46. Thus, in the fourth embodiment, by this ratchet mechanism, the element wires 8 at the tip can be steppedly fixed as expanded to be of a fan shape of any size. By the way, this ratchet mechanism may be unlocked by pulling the trigger part 52 of the locking member 46 toward the holding side.

The effects of this fourth embodiment are substantially the same as of the above mentioned first embodiment.

Figure 9:
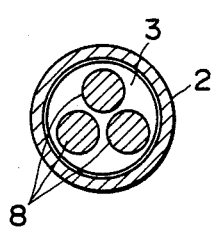
FIG. 9 is a sectioned view showing the part containing the element wires in the fifth embodiment of the present invention.

FIG. 9 shows the element wires in the fifth embodiment of the present invention as contained.

In the first embodiment shown in FIG. 1, the element wires 8 are contained as arranged in the same plane within the sheath 2, whereas, in this fifth embodiment, they are contained as bundled so as to be positioned, for example, at the respective apices of an equilateral triangle as regulated by the inner peripheral wall of the sheath instead of being arranged in the same plane. On the other hand, in case the element wires 8 are released and expanded, they will expand in the same plane. The others are the same as of the above mentioned first embodiment. By the way, in the case of others than the three element wires 8, a plurality of element wires 8 may be contained as bundled or closely collected within the sheath 2. Thus, the sheath 2 may be of a smaller diameter and the thrusting hole may be smaller.

In the above mentioned respective embodiments, the movable shaft 3 may be provided with a key or pin so as not to rotate and, on the other side, the sheath 2, operating part body 4 or the like may be provided with a key groove.

Also, in the above mentioned respective embodiments, the shaft side is made slidable with respect to the sheath but the shaft may be fixed and the sheath side may be made slidable.

In the above mentioned respective embodiments, the element wires are to be expanded in the same plane but are not limited to be in the same plane and may be expanded three-dimensionally on such curved surface as, for example, a conical surface, polygonal conical surface or cylindrical surface. Linear or rod-shaped members may be used instead of the element wires. By the way, the present invention can be used not only to assist the observation but also, for example, to assist the treatment.

According to the above described respective embodiments, as a plurality of element wires given a characteristic of expanding in the same plane can be advanced out of and retracted into the sheath, by controlling their projected amount, even organs of different sizes can be moved aside by a simple operation so as not to obstruct the observation and an organ desired to be observed can be set in a state easy to observe.

Figure 10:
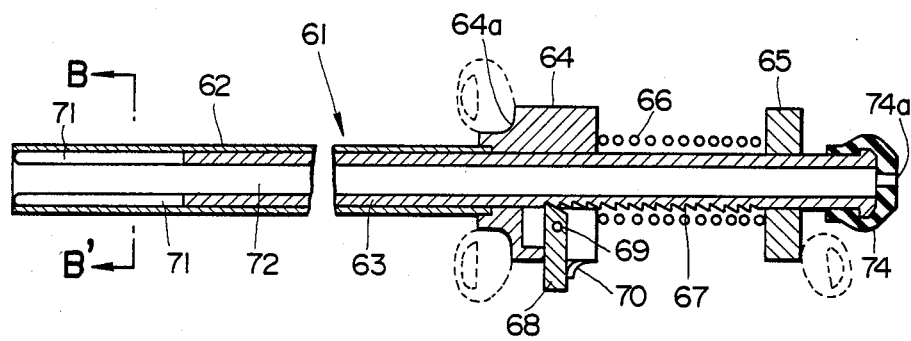
FIGS. 10 to 12 relate to the sixth embodiment of the present invention.

FIG. 10 shows the sixth embodiment of the present invention.

The sixth embodiment shows a removing apparatus for removing an organ obstructing the observation.

In a removing apparatus 61 of this embodiment, a hollow inner tube 63 as a moving member is slidably inserted through an elongate hollow outer tube 62 having an outside diameter insertable through a trocar not illustrated. An operating part body 64 having a hollow part through which the inner tube 63 is insertable is provided as connected to the rear end of the above mentioned outer tube 62. A finger resting part 64a is formed in the front end part of this operating part body 64. For example, a thick cylindrical operating member 65 on which a finger can be rested is secured to the outer peripheral part on the rear end side of the above mentioned inner tube 63. Such spring 66 as a coil spring energizing the operating member 65 rearward with respect to the operating part body 64 is fitted between the front end of this operating member 65 and the rear end of the above mentioned operating part body 64. An operating means moving the inner tube 63 in the axial direction is formed of the operating part body 64, operating member 65 and spring 66.

Ratchet grooves 67 are formed in the axial direction from the position in which the above mentioned operating member 65 is secured to the half way on the tip side in the outer peripheral part of the above mentioned inner tube 63. On the other hand, the above mentioned operating part body 64 is incised in a part on the rear end side and a ratchet pawl 68 engageable with the above mentioned ratchet grooves 67 is provided in this incised part, is rotatably borne on the operating part body 64 by a rotary shaft 69, is energized in the clockwise direction by a plate spring 70 secured to the operating part body 64, is regulated in the clockwise rotation by the operating part body 64 and is normally engaged with the above mentioned ratchet groove 67 so as to be able to regulate the movement of the above mentioned inner tube 63 and fix the inner tube 63 in any position with respect to the outer tube 62.

Figure 11:
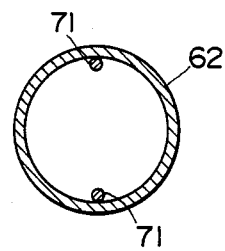

As shown in FIG. 11, for example, two removing members 71 each made of a round rod-shaped elastic material formed to be spherical at the tip are secured to the tip of the above mentioned inner tube 63. These removing members 71 are energized to be linear along the inner wall of this outer tube 62 when they are thrust into the above mentioned outer tube 62 from the tip of the outer tube 62 by the movement of the above mentioned inner tube 63 and to expand on the tip side as shown in FIG. 2 when they are projected out of the tip of the outer tube 62. By freely setting the projected amount out of the tip of the outer tube 62 of these removing members 71, the expanded amount of the removing members 71 can be freely varied and set.

A treating device path 72 is formed of the hollow part of this inner tube 63 through the above mentioned inner tube 63. A rubber cap 74 having a treating device inserting port 74a and keeping air-tightness in case a treating device 75 is inserted through the above mentioned treating device path 72 is provided at the rear end of this inner tube 63.

Figure 12:
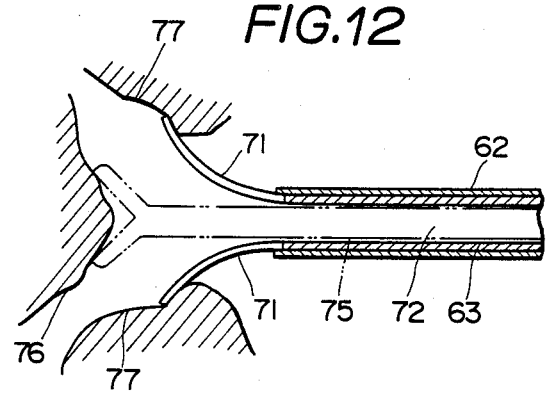

The functions of the embodiment by the above formation shall be explained in the following with reference to FIG. 12.

For example, in the case of a treatment with the treating device under the observation with an endoscope not illustrated inserted into a body cavity through a trocar not illustrated, the treating device 75 is inserted through the treating device path 72 within the inner tube 63 of the removing apparatus 61 of this embodiment, the removing members 71 are thrust into the outer tube 62 and this removing apparatus 61 is inserted into the body through another trocar not illustrated. The above mentioned treating device 75 is projected out of the tips of the inner tube 63 and outer tube 62 to treat an object position 76. In the case of this treatment, if a tissue 77 around the object position obstructs the progress of the treating device 75 and the treatment, the operating member 65 will be operated to move to the tip side with respect to the operating part body 64 against the spring 66 to move the inner tube 63 to the tip side with respect to the outer tube 62. Thereby, the removing member 71 will project out of the tip of the outer tube 62 and will expand on the tip sides. The surrounding tissue 77 obstructing the treatment of the object position 76 will be able to be moved aside with the expanded removing members 71 and the treatment with the treating device 75 will be able to be easily made.

In this embodiment, the inner tube 63 can be fixed in any position with respect to the outer tube 62 with the ratchet mechanism by the ratchet grooves 67 and ratchet pawl 68. The expanded amount of the removing members 71 can be freely set in response to the tissue to be removed by freely setting the projected amount of the above mentioned removing members 71 out of the tip of the outer tube 62.

In the case of retracting the above mentioned removing members 71 into the outer tube 62 or reducing the expanded amount of these removing members 71, the ratchet pawl 68 is rotated counterclockwise against the energizing force of the plate spring 70 to disengage the ratchet pawl 68 with the ratchet groove 67. Then, the inner tube 63 will be moved rearward by the energizing force of the spring 66 and the removing members 71 will be retracted into the outer tube 62.

Thus, according to the sixth embodiment, as the treating device 75 can be inserted through the treating device path 72 within the inner tube 63, through one trocar, while the tissue or organ obstructing the treatment is removed, the object position can be variously treated and, therefore, the damage given to the patient can be reduced. The removal of the tissue or organ obstructing the treatment and the treatment with the treating device can be made even by one person under the observation with an endoscope and the efficiency of the treatment and the workability are high.

Figure 13:
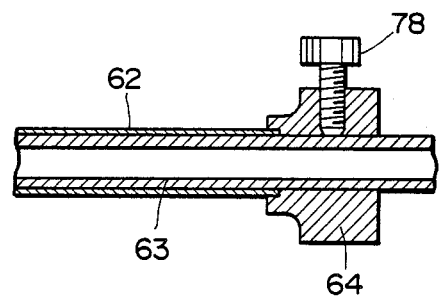
FIG. 13 is a sectioned view of the operating part body surroundings, showing a modification example of the sixth embodiment.

In this embodiment, the inner tube 63 is fixed with respect to the outer tube 62 by means of the ratchet mechanism by the ratchet groove 67 and ratchet pawl 68. However, as shown in FIG. 13, the inner tube 63 may be fixed with a fixing screw 78 passing through to the hollow part from the outer periphery of the operating part body 64.

The moving member is not limited to be the inner tube 63 but may be, for example, a rod-shaped member movable along the inner wall of the outer tube 62.

The shape of the removing member 71 is not limited to be a round rod shape but may be, for example, a plate shape or cylindrical shape provided with a plurality of slits on the tip side. The number of the removing members is not limited to be two but may be one or three or more.

If a cock opening and closing the treating device path 72 is provided in addition to the rubber cap 74 keeping airtightness in inserting the treating device, the airtightness will be further secured.

The spring 66 is not limited to be the coil spring but may be a plate spring or the like. Also, the spring energizing the ratchet pawl 68 in the clockwise direction is not limited to be the plate spring 70 but may be, for example, a twisted coil spring provided around the rotary shaft 69.

Figure 14:
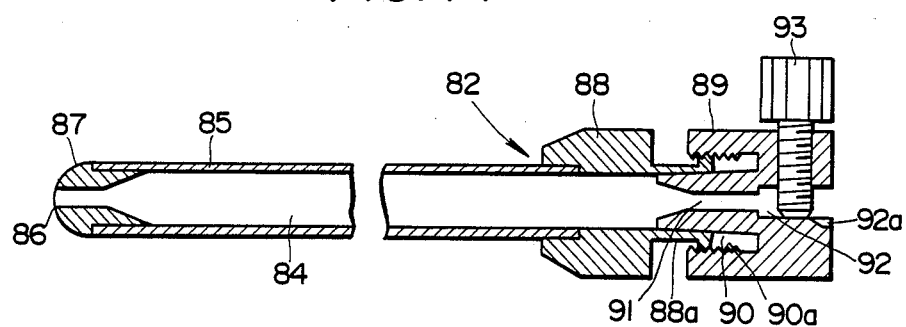
FIGS. 14 to 16 relate to an example of a disposing apparatus used in combination with the removing apparatus of the present invention.
Figure 15:
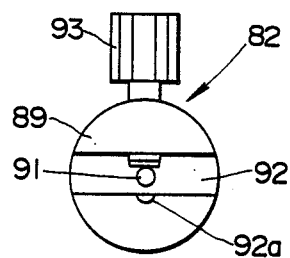
Figure 16:
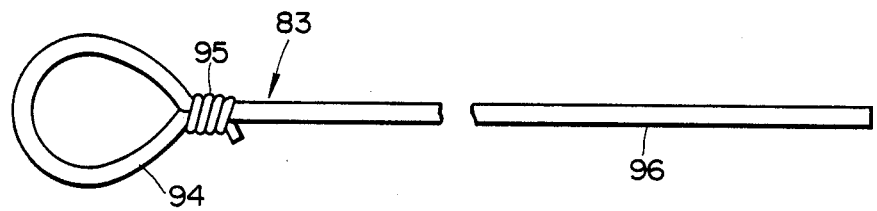

An example of various treating devices to be used in combination with the removing apparatus 61 of this embodiment is such binding apparatus as is shown in FIGS. 14 to 16.

A binding thread holder 82 is provided with a hollow insertion tube 45 having a binding thread path 84 inside. A tip member 87 having a tip side inserting hole 86 communicating with the above mentioned binding thread path 84 is secured on the tip side of this insertion tube 85. The tip surface of this tip member 87 is formed to be spherical. The inside diameter of the above mentioned tip side inserting hole 86 is made smaller than the inside diameter of the above mentioned binding thread path 84.

On the other hand, a front body 88 having a hollow part communicating with the above mentioned binding thread path 44 is provided as connected to the rear end side of this insertion tube 85. A lure lock-shaped connecting part 88a is formed in the rear end part of this front body 88. A rear body 89 is removably connected to this lure lock-shaped connecting part 88a. A groove part 90 annular in the cross-section into which the above mentioned lure lock-shaped connecting part 88 is to be inserted is provided in the axial direction on the tip side of this rear body 89. A female screw 90a is made on the inside surface of this groove part 90. The above mentioned lure lock-shaped connecting part 88a is screwed with this female screw 90a to connect the rear body 89 and front body 88 with each other. This rear body 89 is provided in turn from the tip side with a holding side inserting hole 91 communicating with the above mentioned binding thread path 84 and a slit 92. As shown in FIG. 15, a guide groove 92a for positioning the binding thread 83 is provided below the central part of the slit 92. Further, this rear body 89 is provided with a fixing screw 93 passing through to the above mentioned slit 92 from the outer peripheral part so as to be able to hold and fix the binding thread 83 between the tip surface of this fixing screw 93 and the end surface of the slit 92.

As shown in FIG. 16, the above mentioned binding thread 83 consists of one thread bound to form a ring 94 on the tip side. A knot 95 is formed to be of such size as does not pass through the tip side inserting hole of the above mentioned binding thread holder 82. When the binding thread is pulled on the holding side 96 with the knot 95 fixed, the size of the above mentioned ring 94 will contract.

In binding with this binding device, first of all, the binding thread 43 is inserted on the holding side 96 through the binding thread path 84 from the tip side inserting hole 86, is further passed through the holding side inserting hole 91 and slit 92 and is then pulled out of the rear end of the rear body 89. With the ring 94 of this binding thread projected out of the tip of the tip member 87, the binding thread 83 is positioned on the holding side 96 with the guide groove 92a and is fixed with the fixing screw 93.

In this state, the insertion tube 85 is inserted through the treating device path 72 of the removing apparatus 86 of the sixth embodiment to lead the binding thread 83 into a body cavity. The ring 94 of the above mentioned binding thread 83 is applied to surround a position (not illustrated) required to be bound to stop bleeding or the like. Then, the rear body 89 is rotated with respect to the front body 88 to be removed from the front body 88. Then, this rear body 89 is pulled to pull the binding thread 83 fixed to this rear body 89 with the above mentioned screw 93. Then, as the knot 95 of this binding thread 83 can not pass through the tip side inserting hole 86, the knot 95 will be locked with the tip member 87, the ring will become gradually smaller and the position (not illustrated) required to be bound will be able to be bound.

It is needless to say that this binding device can be inserted directly into a body cavity through a trocar or the like.

Further, the removing apparatus of the sixth embodiment can be used in combination with not only the above mentioned binding device but also such various treating devices as forceps, bleeding stopping devices and incising devices.

Now, there is a case that an ovary is observed by using the above mentioned first embodiment to make fertilization outside the body. In such case, a salpinx is grasped and lifted to make it easy to bed a fertilized egg in a salpinx cluster.

In the case of the above mentioned treatment, grasping forceps have been generally used. However, in case an ovary or the like is held, it will be likely to be collapsed or hurt. Therefore, if the grasping apparatus shown in FIG. 7 is used, such disadvantage can be avoided.

In this grasping apparatus 101, a connecting member 103 having a hollow part communicating with a hollow part of an elongate sheath 102 is provided as connected to the rear end of the sheath 102. A tapered recess 103a is formed in the rear end part of this connecting member 103 and an operating part body 104 as an operating part having on the tip side a projection 104a fitting in this recess 103 is removably connected to the rear end part of the connecting member 103. In this operating part body 104, two slots 105a and 105b communicating with the hollow part of the above mentioned sheath 102 are formed in the axial direction so as to be substantially parallel in the lengthwise direction.

A band-shaped member 106 is inserted through the above mentioned sheath 102. This band-shaped member 106 is inserted at both ends 106a and 106b respectively through the above mentioned slots 105a and 105b, is led out of the rear end of the operating part body 104, is inserted in the course through the sheath 102 and is projected out of this sheath 102 to form a loop-shaped grasping part 107. This band-shaped member 106 is formed of a metal plate, such resin as Teflon (trade name) or rubber.

A screw hole 108 passing through to the slot 105a from the outer peripheral part of this operating part body 4 is provided in the side part of one slot 105a side of the above mentioned operating part body 104. A fixing screw 109 is screwed in this screw hole 108 to press and fix on the tip surface one end part 106a side of the band-shaped member 106 inserted through the slot 105a.

An incision 110 reaching this slot 105b is formed in the side part of the other slot 105 side of the above mentioned operating part body 104. A lever 112 rotatably borne by a pin 11 on this operating part body 104 is provided in this incision 110. This lever 112 projects at one end out of the side of the operating part body 104 to form a finger resting part 112a so that, when this finger resting part 112a is pulled toward the holding side to rotate the lever 112 counterclockwise, the pressing part 112b of the lever 112 on the opposite side of the pin 111 will be able to press and fix the other end part 106b side of the band-shaped member 106 inserted through the slot 105b.

When the band-shaped member 106 fixed on one end part 106a side with the above mentioned fixing screw 109 is moved on the other end part 106b side in the axial direction, the size of the loop of the grasping part 107 projected out of the tip of the sheath 102 will be able to be varied. When the band-shaped member 106 is fixed on the other end part 106b side with the above mentioned lever 112, the size of the loop of the above mentioned grasping part 107 will be able to be maintained at any size.

A pin 113 is provided in the diametral direction on the tip side of the hollow part of the above mentioned sheath 102. The above mentioned band-shaped member 106 passes on both sides of this pin 113 so that, in case this band-shaped member 106 is pulled in the other end part 106b, it will not be pulled into the sheath 102 by more than a predetermined amount.

The functions of the embodiment by the above formation shall be explained in the following with reference to FIG. 18.

Figure 18:
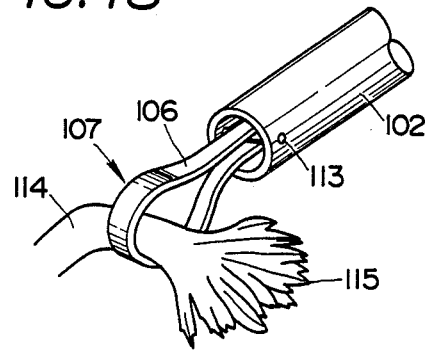

In FIG. 18, the reference numeral 114 represents a salpinx and 115 represents a salpinx cluster.

For example, in the case of grasping and lifting the salpinx 114 to bed an egg fertilized outside the body in the salpinx cluster 115, the loop of the grasping part 107 is made small enough and the grasping apparatus 101 is inserted into the body cavity through a trocar (not illustrated) or the like. Then, the band-shaped member 106 is fixed on one end part 106a side with the fixing screw 109 and is moved on the other end part 106b side in the axial direction to set the size of the loop of the grasping part 107 at a proper size. Then, under the observation with an abdominal cavity endoscope, the salpinx 114 is inserted through the loop of the above mentioned grasping part 107 from the salpinx cluster 115 side. Then, the band-shaped member 106 is pulled on the other end part 106b side to make the loop of the above mentioned grasping part 107 smaller. Further, the finger resting part 112a of the lever 112 is pulled to fix the band-shaped member 106 on the other end part 106b side and to maintain the size of the loop of the grasping part 107 as fixed. Meanwhile the salpinx 114 is lifted.

According to this grasping apparatus, as the loop-shaped grasping part 107 is formed of the band-shaped member 106 and the area of the grasping part 107 in contact with the salpinx 114 is wide, the grasping part 107 will not be forced into the salpinx 114 or will not hurt it and, as the salpinx 114 is grasped on the entire periphery by the loop-shaped grasping part 107, it will be able to be positively grasped.

Figure 19:
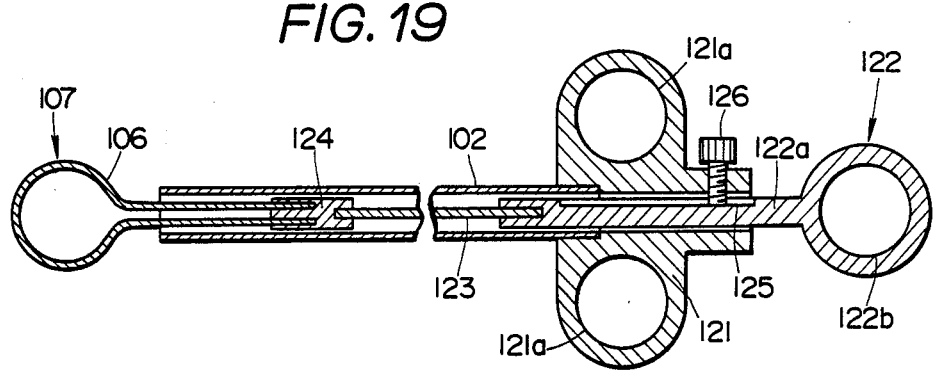
FIG. 19 is a sectioned view of a grasping apparatus of the second embodiment.

FIG. 19 shows the second embodiment of the grasping apparatus. In this grasping apparatus, an operating part body 121 having a hollow part communicating with the hollow part of a sheath 102 and having two finger resting parts 121a formed is provided as connected to the rear end of the sheath 102. A shaft part 122a of a sliding member 122 having a finger resting part 122b on the rear end side of the shaft part 122a is slidably inserted through the hollow part of this operating part body 121. A rod-shaped connecting member 123 is connected to the tip of the shaft part 122a of this sliding member 122. A columnar moving member 124 is connected to the tip of this connecting member 123 and is made to slide in the axial direction through the sheath 102 when the above mentioned sliding member 122 is slid in the axial direction. A band-shaped member 106 projecting out of the tip of the sheath 102 to form a loop-shaped grasping part 107 is secured at both ends to the tip side of this moving member 124. A key groove 125 is formed in the axial direction on one side of the shaft part 122a of the above mentioned sliding member 122. A fixing screw 126 passing through to the hollow part from the outer peripheral part of the operating part body 121 on this key groove 125 side is fitted in the tip part into this key groove 125. By fastening this screw 126, the above mentioned sliding part 122 can be fixed in any position.

In this embodiment, by loosening the fixing screw 126 and moving the sliding member 122 in the axial direction with respect to the operating part body 121, the size of the loop of the grasping part 107 can be set at any size and, by fastening the fixing screw 126, the sliding member 122 can be fixed to maintain the size of the loop of the grasping part 107 as fixed.

Further, in this embodiment, by loosening and removing the fixing screw 126 completely from the key groove 125, all the members inserted through the sheath 102 can be pulled out of the sheath 102 and it is easy to wash the interior of the sheath 102.

By the way, the sliding member 122 may be fixed in any position by means of a ratchet mechanism or the like instead of the key groove 125 and fixing screw 126.

Figure 20:
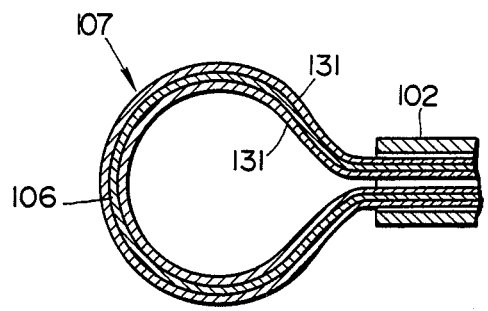
FIG. 20 is a sectioned view of the tip side of a grasping apparatus of the third embodiment.

FIG. 20 is a sectioned view of the tip side of the third embodiment of the grasping apparatus.

In this embodiment, a band-shaped member 106 made of a metal is coated with such elastic material as such resin as Teflon (trade mark) or rubber.

If the band-shaped member 106 is formed of such elastic material as a resin or rubber, such organ within a body cavity as a salpinx will be less likely to be hurt but it will be difficult to maintain the loop of the grasping part 107 in a proper form. According to the present embodiment, the loop of the grasping part 107 can be maintained in a proper form and such organ within a body cavity as a salpinx or the like can be made less likely to be hurt.

By the way, the band-shaped member 106 may be formed by arranging a plurality of such cores as fine metal wires and providing an elastic material around them.

Figure 17:
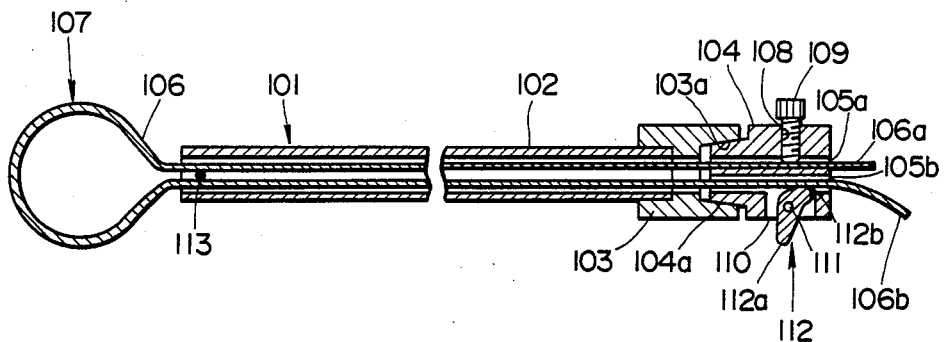
FIGS. 17 and 18 relate to the first embodiment of a grasping apparatus.

The other functions and effects are the same as of the one shown in FIG. 17.

Figure 21:
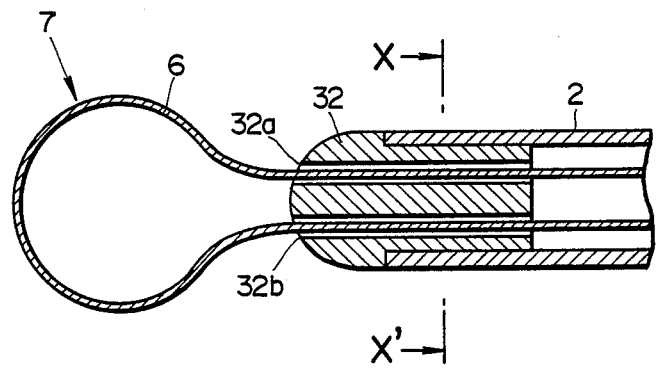
FIGS. 21 and 22 relate to the fourth embodiment of a grasping apparatus.
Figure 22:
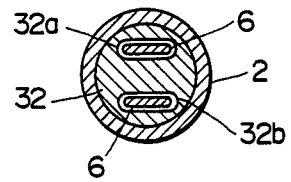

FIG. 21 shows the tip side of the fourth embodiment of the grasping apparatus.

In this embodiment, a columnar protective member 132 formed to be hemispherical on the tip surface is fitted to the tip of a sheath 102. Two slots 132a and 132b through which the band-shaped member 106 is to be inserted are formed in the axial direction in this protective member 132. The band-shaped member 106 is inserted through these slots 132a and 132b and is projected out of the tip surface of the protective member 132.

According to this embodiment, in case such soft organ within a body cavity as a salpinx is grasped by the grasping part 107, this organ will be able to be prevented from being hurt by colliding with the tip part of the sheath 102 or by being pulled into the sheath.

The other functions and effects are the same as of the one shown in FIG. 17.

In the above mentioned grasping apparatus, the sheath 102 may be flexible or rigid, may be inserted into a body cavity through a trocar or the like from the body surface or may be inserted into the body cavity through a treating device channel of a flexible endoscope from a mouth cavity or the like.

What is claimed is:

1. Observation assisting forceps for assisting the observation with an endoscope provided with an observing means and an insertion part insertable into a body cavity comprising:
    a hollow sheath;
    a shaft-shaped member inserted through said sheath for extension therethrough into a maximum extended position and retraction therein into a maximum retracted position;
    an operating part formed on the rear end side of said shaft-shaped member and having a shaft-shaped member moving means formed therein;
    an observation assisting piece consisting of a plurality of linear members fitted in rear end bases to the front end side of said shaft-shaped member and given such characteristic as of expanding on the tip sides and substantially spherical parts formed at the tips of said respective linear members; and
    a fixing means in said moving means for fixing said shaft-shaped member at selected positions intermediate said maximum extended position and said maximum retracted position in said hollow sheath.

2. Observation assisting forceps according to claim 1 wherein said plurality of linear members are given a characteristic of expanding in the same plane on the tip side.

3. Observation assisting forceps according to claim 1 wherein said plurality of linear members are given a characteristic of expanding in the courses to the tip parts and the tip parts are parallel with one another.

4. Observation assisting forceps according to claim 1 wherein said plurality of linear members are given a characteristic of three-dimensionally expanding to form a conical surface or polygonal conical surface.

5. Observation assisting forceps for assisting the observation with an endoscope provided with an observing means and an insertion part insertable into a body cavity comprising:
    a hollow sheath;
    a shaft-shaped member inserted through said sheath for extension therethrough into a maximum extended position and retraction therein into a maximum retracted position;
    an operating part formed on the rear end side of said shaft-shaped member and having a shaft-shaped member moving means formed therein;
    an observation assisting piece consisting of a plurality of linear members fitted in the rear end bases to the front end side of said shaft-shaped member and given such characteristic as of expanding on the tip sides and substantially spherical parts formed at the tips of said respective linear members; and
    a fixing means in said moving means for fixing said shaft-shaped member at selected positions intermediate said maximum extended position and said maximum retracted position in said hollow sheath, said moving means including a ratchet mechanism for fixing said shaft-shaped member in said selected positions.

6. Observation assisting forceps according to claim 1 wherein said sheath is of such inside diameter as can contain said plurality of linear members as bundled.

* * * * *